(12) United States Patent
Nakamura et al.

(10) Patent No.: US 8,147,425 B2
(45) Date of Patent: Apr. 3, 2012

(54) CENTESIS INSTRUMENT

(75) Inventors: Toshihisa Nakamura, Ashigarakami-gun (JP); Daisuke Nishiuchi, Ashigarakami-gun (JP); Yoshiaki Yaguchi, Ashigarakami-gun (JP); Masao Takinami, Nakakoma-gun (JP)

(73) Assignee: Terumo Kabushiki Kaisha, Tokyo (JP)

( * ) Notice: Subject to any disclaimer, the term of this patent is extended or adjusted under 35 U.S.C. 154(b) by 1152 days.

(21) Appl. No.: 11/887,474

(22) PCT Filed: Mar. 20, 2006

(86) PCT No.: PCT/JP2006/305599
§ 371 (c)(1), (2), (4) Date: Sep. 28, 2007

(87) PCT Pub. No.: WO2006/109452
PCT Pub. Date: Oct. 19, 2006

(65) Prior Publication Data
US 2009/0275860 A1 Nov. 5, 2009

(30) Foreign Application Priority Data
Mar. 31, 2005 (JP) ................................ 2005-102343

(51) Int. Cl.
*A61B 5/00* (2006.01)
*A61B 17/14* (2006.01)
*A61B 17/32* (2006.01)
(52) U.S. Cl. .................. 600/583; 606/181; 606/182
(58) Field of Classification Search .................. 600/573, 600/576, 578, 579, 583, 584; 606/181, 182
See application file for complete search history.

(56) References Cited

U.S. PATENT DOCUMENTS
5,366,470 A 11/1994 Ramel
(Continued)

FOREIGN PATENT DOCUMENTS
JP 7-500995 A 2/1995
(Continued)

OTHER PUBLICATIONS

Official Action issued on Sep. 13, 2011 by the Japanese Patent Office in corresponding Japanese Patent Application No. 2007-512449, and partial English language translation of the Official Action.

(Continued)

*Primary Examiner* — Max Hindenburg
*Assistant Examiner* — Adam Eiseman
(74) *Attorney, Agent, or Firm* — Buchanan Ingersoll & Rooney PC

(57) ABSTRACT

A centesis instrument, wherein a patient applies a contact part to a palm, a finger, or an arm in the state of gripping an outer tube by hand and presses the outer tube against its measured portion. A third coiled spring is compressed to increase spring power. When the outer tube reaches a prescribed position, the tip face of the vertical portion of a centesis button reaches a hole part, and a projected part is allowed to be pressed. When the patient presses a button body from a direction perpendicular to the axis of the button body by using a finger at that position, a locking piece is separated from a locking part and the centesis needle of a centesis needle unit is instantaneously projected from the opening part of the contact part to the measured portion by the spring power of the third coiled spring for centesis. Thus, a prescribed amount of blood can be taken out from the measured portion.

14 Claims, 10 Drawing Sheets

U.S. PATENT DOCUMENTS

| | | | |
|---|---|---|---|
| 5,964,718 A * | 10/1999 | Duchon et al. | 600/583 |
| 6,461,496 B1 * | 10/2002 | Feldman et al. | 205/777.5 |
| 7,060,192 B2 | 6/2006 | Yuzhakov et al. | |
| 7,169,116 B2 * | 1/2007 | Day et al. | 600/583 |
| 2002/0002344 A1 * | 1/2002 | Douglas et al. | 600/583 |
| 2003/0083686 A1 * | 5/2003 | Freeman et al. | 606/181 |
| 2003/0191415 A1 * | 10/2003 | Moerman et al. | 600/584 |
| 2003/0223906 A1 | 12/2003 | McAllister et al. | |
| 2004/0215224 A1 | 10/2004 | Sakata et al. | |
| 2006/0259058 A1 * | 11/2006 | Schiff et al. | 606/181 |
| 2008/0119884 A1 * | 5/2008 | Flora et al. | 606/182 |

FOREIGN PATENT DOCUMENTS

| | | |
|---|---|---|
| JP | 11-164825 A | 6/1999 |
| JP | 2000-511068 | 8/2000 |
| JP | 2000-245717 A | 9/2000 |
| JP | 2001-309905 A | 11/2001 |
| JP | 2002-65648 A | 3/2002 |
| JP | 2002-219114 A | 8/2002 |
| JP | 2003-102712 A | 4/2003 |
| JP | 2004-33759 A | 2/2004 |
| JP | 2004-113772 A | 4/2004 |
| WO | WO 97/42886 A1 | 11/1997 |
| WO | WO 03/007819 A1 | 1/2003 |

OTHER PUBLICATIONS

Official Action dated Jun. 28, 2011, issued by the Japanese Patent Office in corresponding Japanese Patent Application No. 2007-512449, and partial English language translation of the Official Action.

* cited by examiner

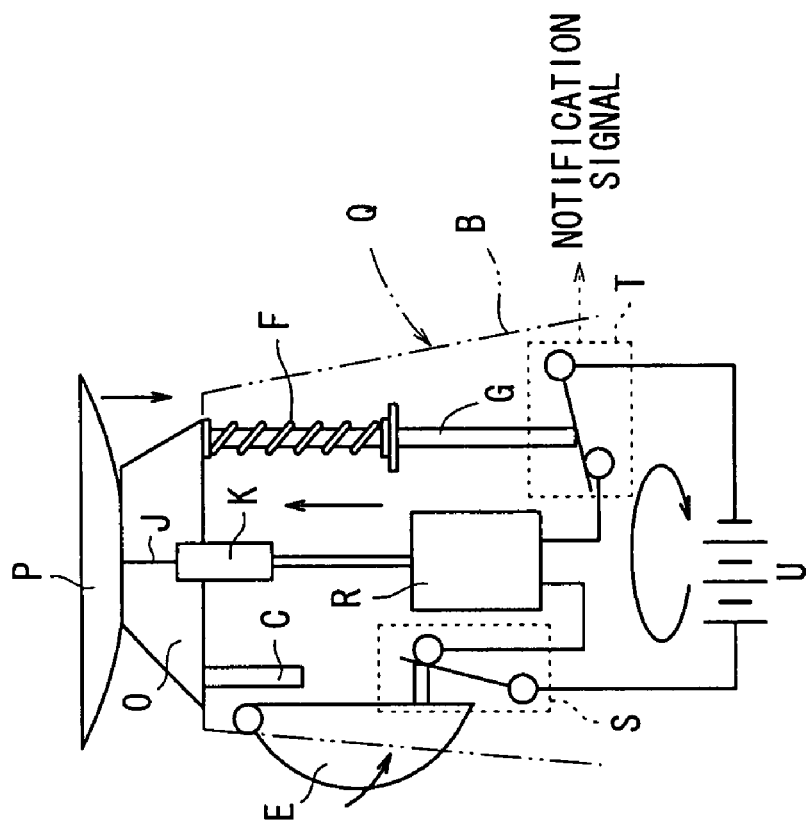
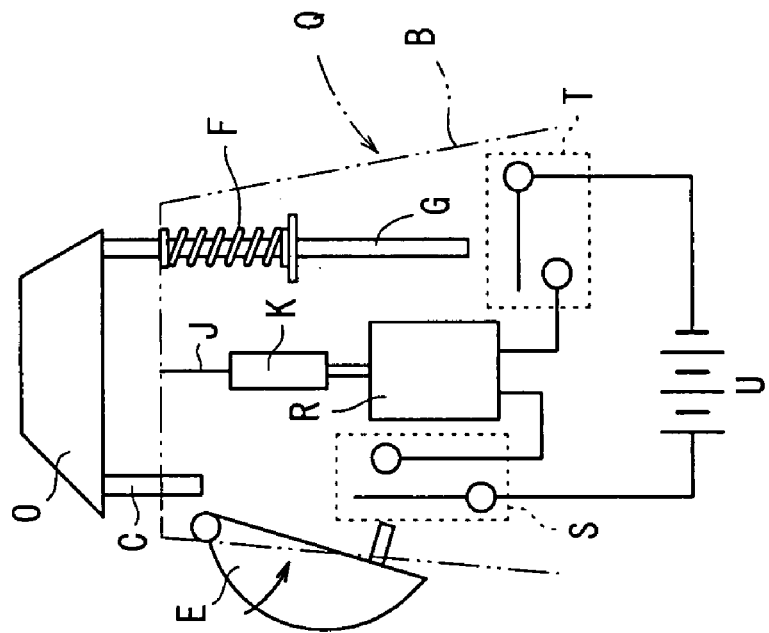

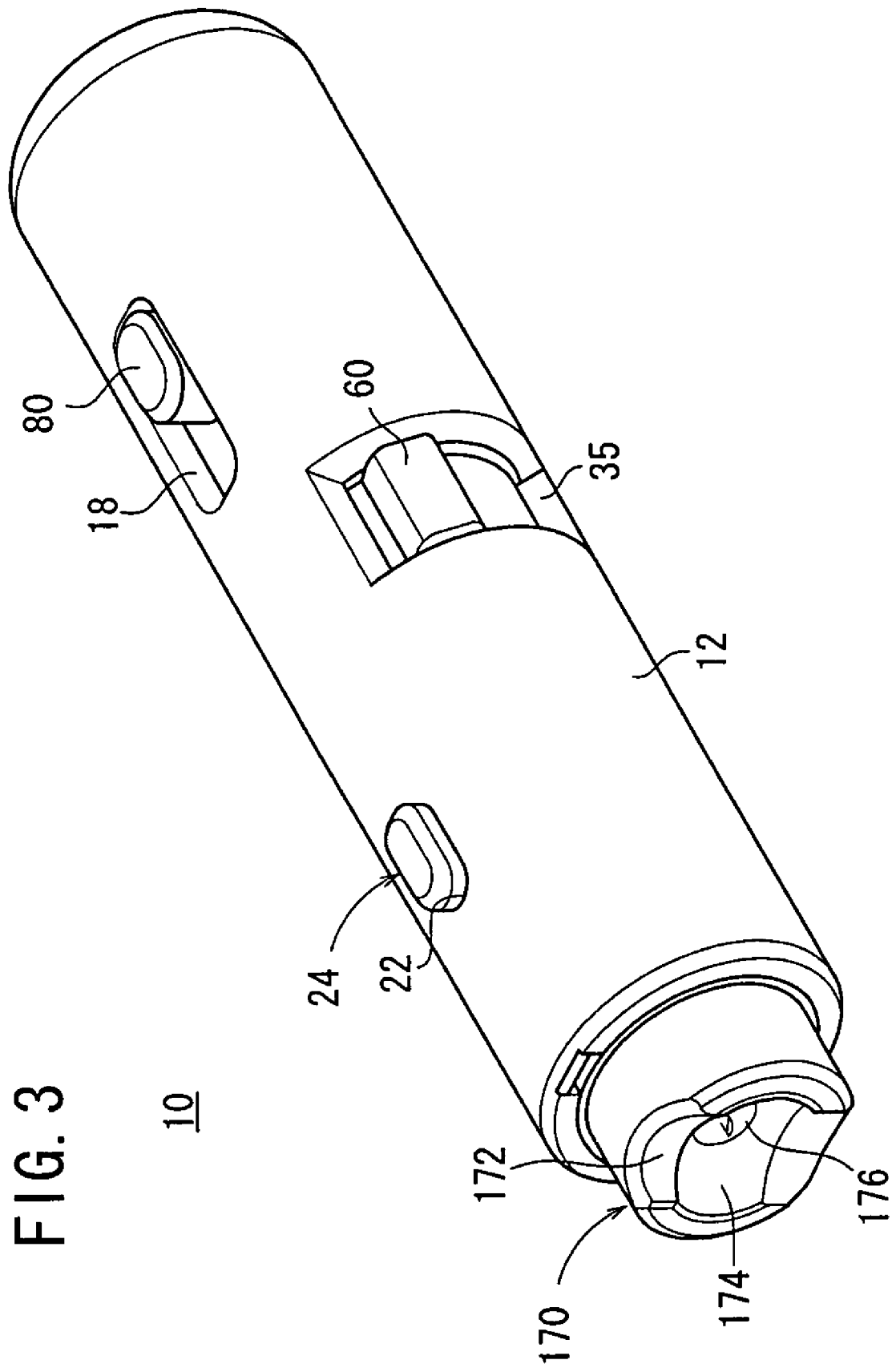

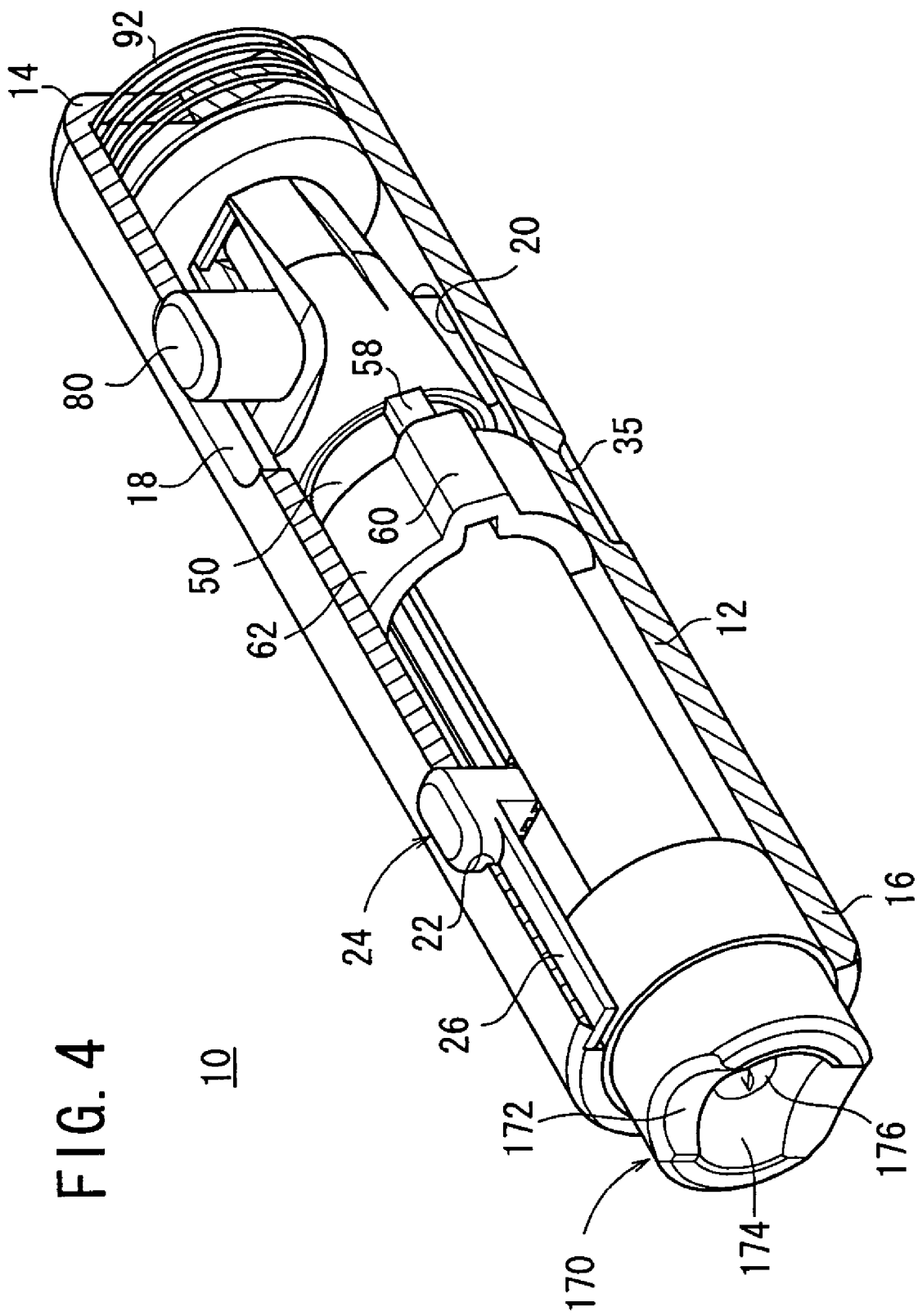

CENTESIS INSTRUMENT

TECHNICAL FIELD

The present invention relates to a puncture instrument (centesis instrument), and more particularly to a puncture instrument for obtaining a predetermined amount of blood from a patient by pushing the distal end of the puncture instrument against the skin of the patient and puncturing the skin with the distal end.

BACKGROUND ART

It is recommended that diabetic patients measure their own blood glucose level by measuring its variations by themselves for their daily self-care. A blood glucose level is measured by preparing a test paper impregnated with a reagent which gives a color depending on the amount of glucose in blood, supplying blood to the test paper to cause the test paper to produce a color, and optically measuring the degree of the color for displaying the blood glucose level.

According to a blood component measuring device which is used for the above purpose, when the patient is to take a blood sample of its own, the patient uses a blood component measuring tip having an axially movable puncture needle. Under repulsive forces from an elastic body, the puncture needle is instantaneously forced to project toward and puncture the skin, letting a small amount of blood come out onto the skin.

If the blood component measuring tip is combined with a test paper, then the blood that has permeated in the test paper can optically be measured effectively. The blood component measuring device of this kind is capable of continuously and automatically performing the puncturing process and the measuring process. Accordingly, the blood component measuring device can measure the blood accurately and reliably within a short time through simple operation.

The present applicant has already proposed an invention "Component measurement device" (Japanese Laid-Open Patent Publication No. 2001-309905) in relation to the blood component measuring device.

For carrying out self-measuring of blood glucose, a blood glucose meter needs to puncture a fingertip or the like of the patient with a puncture needle, sample a small amount of blood, and apply a drop of blood to a sensor. For successful measuring, it is a task of great importance for the patient to obtain a sample of blood stably from the punctured region without the need for any special operation after the patient has punctured the skin with the puncture needle.

DISCLOSURE OF THE INVENTION

It is an object of the present invention to provide a puncture instrument which is capable of performing a puncturing action simply and stably to obtain a desired amount of blood.

To achieve the above object, a puncture instrument according to the present invention comprises a first tube, a second tube mounted in the first tube, a drive mechanism displaceably mounted in the second tube, a puncture needle unit disposed on a distal end of the drive mechanism and having a puncture needle, an abutting member for being pushed against a living body surface, the abutting member being disposed on a distal end of the second tube, and a puncture controller for allowing the puncture needle to puncture the living body surface when a pushing force applied to the living body surface by the abutting member reaches a predetermined value or more.

According to the present invention, when the pushing force applied to the living body surface by the abutting member reaches the predetermined value or more, the puncture needle is allowed to puncture the living body surface. Therefore, the living body such as the doctor, the patient, or the like can puncture the living body surface with the puncture needle stably with security after the living body has confirmed that the puncture needle is allowed to puncture the living body surface.

In the puncture instrument, the puncture controller includes a push button disposed on the first tube and a hole formed in the second tube for allowing the push button to be displaced, and wherein when the push button moves with the first tube along the second tube to the hole, the push button is displaceable into the hole, confirming that a pushing force applied to the living body surface has reached a predetermined value. Based on the confirmation, the patient or the like can operate the puncture instrument to puncture the living body surface reliably with security.

Preferably, the puncture instrument may further comprise a first biasing member disposed in the first tube for biasing the second tube in a direction toward the distal end thereof, a second biasing member disposed in the second tube for displacing the drive mechanism in a direction toward a proximal end thereof, and a third biasing member disposed in the second tube for displacing the drive mechanism in the direction toward the distal end thereof. As the puncture instrument is of a mechanical nature, it can operate to puncture the living body surface stably.

Preferably, the puncture instrument may further comprise a lock mechanism disposed on the drive mechanism for locking the drive mechanism on the second tube against a biasing force of the third biasing member and unlocking the drive mechanism from the second tube. The lock mechanism can keep the puncture instrument reliably in a state allowing the puncture instrument to puncture the living body surface, and also makes it possible to instantaneously cause the puncture instrument to puncture the living body surface.

In the puncture instrument, the lock mechanism may further comprise a pushed member which is capable of abutting against the push button through the hole, and the drive mechanism may comprise an engaging piece which is releasable from an engaging portion of the second tube to allow the drive mechanism to be displaced in the direction toward the distal end when the push button pushes the pushed member. The lock mechanism is simple in structure and allows the puncture instrument to puncture the living body surface reliably.

The puncture instrument may further comprise a notifying unit for notifying that the pushing force applied to the living body surface by the abutting member reaches the predetermined value or more, through at least one of tactile, visual, and auditory sensations. When the notifying unit notifies that the puncture instrument is in a state capable of puncturing the living body surface, the puncture instrument can perform a puncturing action stably and reliably.

If the notifying unit notifies that the pushing force applied to the living body surface by the abutting member reaches the predetermined value or more, through the tactile sensation based on a change in sliding resistance between the push button and the second tube, then it can be confirmed that the puncture instrument is in the state capable of puncturing the living body surface, with a hand gripping the first tube.

The puncture controller may further comprise a puncture button disposed on the first tube and an electric control mechanism for controlling displacement of the drive mechanism. The electric control mechanism makes it possible to realize reliably that the puncture instrument is in the state capable of puncturing the living body surface.

If the electric control mechanism further comprises a first switch for opening and closing an electric circuit depending on the position to which the second tube is displaced, a second switch actuatable by the puncture button, and an actuator for displacing the drive mechanism, then the puncture instrument has a simple structure for performing a puncturing action.

According to the present invention, as the pushing force required to push the abutting member, which has an annular (preferably conical) distal end, against the living body surface can be maintained (guaranteed), the puncture instrument is capable of obtaining a sufficient amount of blood required for measurement even when the living body surface is punctured to a small depth for minimizing pain.

According to the present invention, furthermore, after having realized the timing to puncture the living body surface with the puncture needle, the patient can puncture the living body surface stably and reliably with ease.

A small amount of blood obtained from the skin of the patient which is punctured with the puncture needle is supplied to a test paper to be impregnated therewith, which is used to read the blood glucose level of the blood.

The puncture instrument may further comprise a continuous pushing prompter for prompting the user to keep the abutting member pushed against the living body surface until an appropriate amount of blood seeps out of the living body surface after the living body surface is punctured.

BRIEF DESCRIPTION OF THE DRAWINGS

FIG. 2A is a schematic view of a puncture instrument structure including an electric structure prior to puncture, illustrating the arrangement and operational principles of the puncture instrument according to the exemplary embodiment of the present invention, and FIG. 2B is a schematic view of the puncture instrument structure including the electric structure subsequent to puncture, illustrating the arrangement and operational principles of the puncture instrument according to the exemplary embodiment of the present invention;

FIG. 3 is a perspective view of a puncture instrument according to a first embodiment of the present invention;

FIG. 4 is a perspective view, partly cut away, showing an inner tube of the puncture instrument shown in FIG. 3;

BEST MODE FOR CARRYING OUT THE INVENTION

Figure 1A:
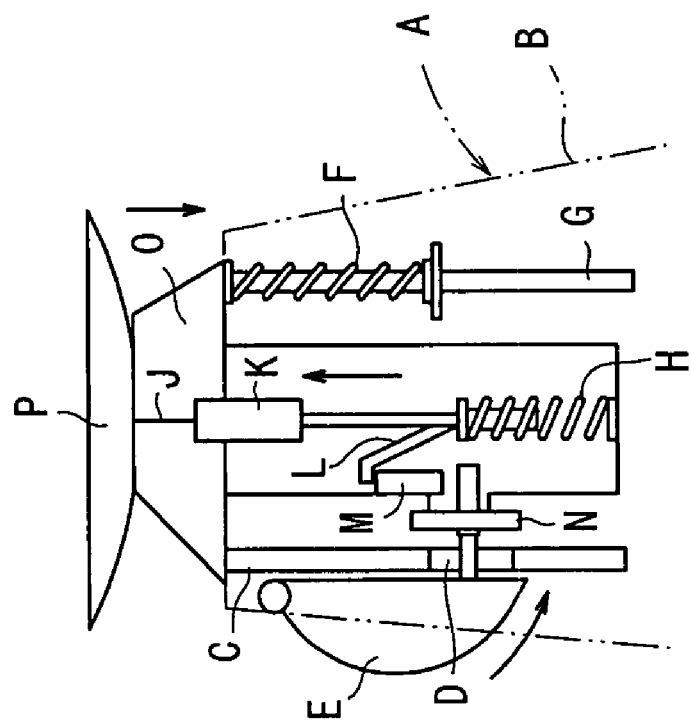
FIG. 1A is a schematic view of a mechanical structure prior to puncture, illustrating the arrangement and operational principles of a puncture instrument according to an exemplary embodiment of the present invention.

A puncture instrument according to a preferred embodiment of the present invention will be described in detail below with reference to the accompanying drawings. Identical reference characters denote identical components throughout views, and those identical components may not be described in detail for the sake of brevity.

FIGS. 1 and 2 show a basic structure of a puncture instrument according to the present invention. The basic structure of the puncture instrument will generally be described below in reference to its operational principles.

FIG. 1 shows the puncture instrument which is pushed against a living body, e.g., a predetermined region such as a hand, a finger, or an arm of the patient, to give a mechanical notification of the arrival at a puncture position. FIG. 2 shows the puncture instrument which gives an electric notification of the arrival at the puncture position.

The puncture instrument A includes a first tube B and a second tube C coaxial with the first tube B. The second tube C has an opening D formed therein with a push button E swingably disposed over the opening D. The second tube C includes a drive member G with a coil spring F coiled therearound and also includes a coil spring H. The coil spring H is coiled around a shaft I supporting on its distal end a puncture needle unit K including a puncture needle J. A bar L is mounted on the shaft I and has its distal end extending so as to be able to ride over a stopper M.

Figure 1B:
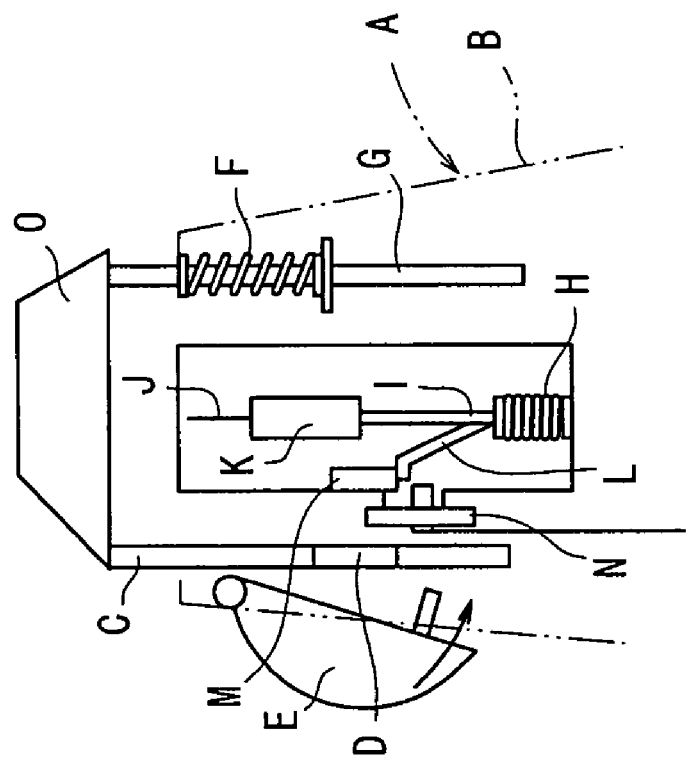
FIG. 1B is a schematic view of a mechanical structure subsequent to puncture, illustrating the arrangement and operational principles of the puncture instrument according to the exemplary embodiment of the present invention.

The second tube C further includes a pushed member N which can be pushed by the push button E. In FIGS. 1A and 1B, the reference character C represents an abutting member to be pushed against the patient, not shown, and P represents a finger of the patient.

FIG. 1A shows the puncture instrument A which is not in a state for puncturing the finger P of the patient, and FIG. 1B shows the puncture instrument A which is in a state wherein the puncture needle J has punctured the finger P of the patient. In FIG. 1A, since the abutting member O has not abutted against the finger P of the patient, the puncture needle unit K including the puncture needle J is present within the first tube B, and the push button E is positioned away from the opening D formed in the second tube C. Therefore, the push button E cannot be turned in the direction indicated by the arrow A of FIG. 1A.

When the patient grips the puncture instrument A and pushes the puncture instrument A against the finger P with the abutting member O interposed therebetween, the abutting member O becomes progressively less spaced from the first tube B until the pin-shaped distal end of the push button E faces the opening D. The patient feels that the push button E faces the opening D, with a finger of the patient which is held in contact with the push button E. When the patient then pushes the push button E, the pin of the distal end of the push button E enters the opening D to push the pushed member N. As a result, the pin of the pushed member N bends the bar L, which rides over the stopper M under the resilient force of the coil spring H. The puncture needle. J instantaneously punctures the finger P of the patient.

FIGS. 2A and 2B show a puncture instrument which is electrically controlled to puncture the finger P of the patient with the puncture needle J, unlike the puncture instrument A that is mechanically controlled to puncture the finger P of the patient as shown in FIG. 1. Those components which are identical to those of the puncture instrument A shown in FIG. 1 are denoted by identical reference characters, and will not be described in detail below.

The puncture instrument Q shown in FIG. 2 differs from the puncture instrument A in that it employs a solenoid R (actuator), a puncture switch S, a detecting switch T, and a power supply U, instead of the coil spring H, the bar L, the stopper M, the pushed member N, etc. shown in FIG. 1.

The puncture instrument Q is in a state shown in FIG. 2 when it does not puncture the finger P of the patient.

Specifically, the puncture switch S is turned off, and the detecting switch T is also turned off. The puncture switch S is a switch for displacing the puncture needle J. The detecting switch T is a switch for detecting that the abutting member O of the puncture instrument Q is pressed against the finger P of the patient, with the puncture instrument Q being in a state capable of puncturing the finger P of the patient.

In the state shown in FIG. 2A, since the detecting switch T is turned off, the power supply U does not supply a current for energizing the solenoid R. When the first tube B is pushed toward the finger P of the patient, the drive member G is displaced relatively with respect to the first tube B and its end turns on the detecting switch T. In the state that the detecting switch T is turned on, it outputs a notification signal. The notification signal serves to notify to the patient that the puncture needle J is in a state capable of puncturing the finger P of the patient. The notification may be made by turning on a display (LCD, LED, EL, or the like), displaying letters, sounding a buzzer, or producing a voice guidance based on artificial voice or the like. At this time, the solenoid R as an actuator is not energized.

When it is notified to the patient that the detecting switch T is turned on through an electric display or voice, the patent pushes and turns the push button E with its finger or the like. When the push button E is turned, the pin of the distal end thereof turns on the puncture switch S. A current is supplied to the solenoid R, which is energized to cause the puncture needle J to project toward and puncture the finger P of the patient.

In the present embodiment, the operation circuit is controlled directly by contact points. However, contact inputs may be judged by a predetermined central processor to control the solenoid in operation.

The puncture instrument A shown in FIG. 1 can mechanically puncture the finger P of the patient to obtain a small amount of blood. The puncture instrument Q shown in FIG. 2 electrically notifies that it can operate to puncture the finger P of the patient, prompting the patient to operate on the push button E to displace the puncture needle J toward the finger P of the patient. The puncture instruments A, Q can perform a puncturing action stably and reliably.

A preferred embodiment of the puncture instrument which has the above operational principles is shown in FIGS. 3 to 9.

In FIGS. 3 to 9, the reference character 10 represents the puncture instrument according to the present embodiment. The puncture instrument 10 includes an outer tube (first tube) 12 having one bottomed end (proximal end) 14 and another open end (distal end) 16. The outer tube 12 has a first oblong hole 18 and a second oblong hole 20 formed therein symmetrically in the diametrical direction of the outer tube 12 near the one end 14 thereof (see FIGS. 6 to 9).

The outer tube 12 also has a third oblong hole 22 formed therein along the axial direction of the first oblong hole 18. A puncture button 24 is displaceably mounted in the third oblong hole 22 (see FIG. 3). The third oblong hole 22 is held in communication with a large recess 23 opening to the inner circumferential surface of the outer tube 12 near the other end 16. As can easily be understood from FIGS. 6 to 9, the puncture button 24 comprises a tongue piece 26 in the shape of a rectangular parallelepiped extending toward the other end 16 of the outer tube 12 and embedded in the outer tube 12, and a button body 28 integrally formed with the tongue piece 26 and having a bent cross-sectional shape. The button body 28 includes a horizontal portion 30 exposed outwardly from the outer tube 12 and a vertical portion 32 extending perpendicularly to the horizontal portion 30 and projecting into an inner bore 34 of the outer tube 12.

The puncture button 24 is preferably located in a position where it is in abutment against an index finger of the patient when the patient grips the outer tube 12.

The outer tube 12 also has a relatively large rectangular fourth oblong hole 35 formed therein between the first oblong hole 18 and the third oblong hole 22 and angularly displaced 900 from the axis interconnecting the first oblong hole 18 and the third oblong hole 22.

An inner tube (second tube) 40 is disposed in the outer tube 12. The inner tube 40 has one end 42 housed in the inner bore 34 of the outer tube 12 and another end 44 exposed out of the other end 16 of the outer tube 12 and having a thick outer circumferential surface positioned by being held in sliding contact with the inner circumferential surface of the other end 16 of the outer tube 12. The inner tube 40 includes a tubular body 46 extending from the other end 44 with a step interposed therebetween inwardly of the other end 44 and having a reduced diameter. The tubular body 46 has a hole 48 formed therein near the puncture button 24. The vertical portion 32 of the puncture button 24 has a horizontal end face slidably held against the outer circumferential surface of the tubular body 46.

The inner tube 40 includes a portion near the one end 42 which is of a reduced diameter smaller than the outside diameter of the tubular body 46. The inner tube 40 has a hollow inner bore 52 held in communication with the hole 48. The inner tube 40 has an engaging portion 54 of triangular cross section which is disposed near the other end 44 of the tubular body 46 and projects into the inner bore 52. A ring-shaped adjusted member 50 is mounted on the one end 42 of the inner tube 40, and a depth adjustment knob 62 is fitted over a portion of the outer circumferential surface of the adjusted member 50.

Figure 5:
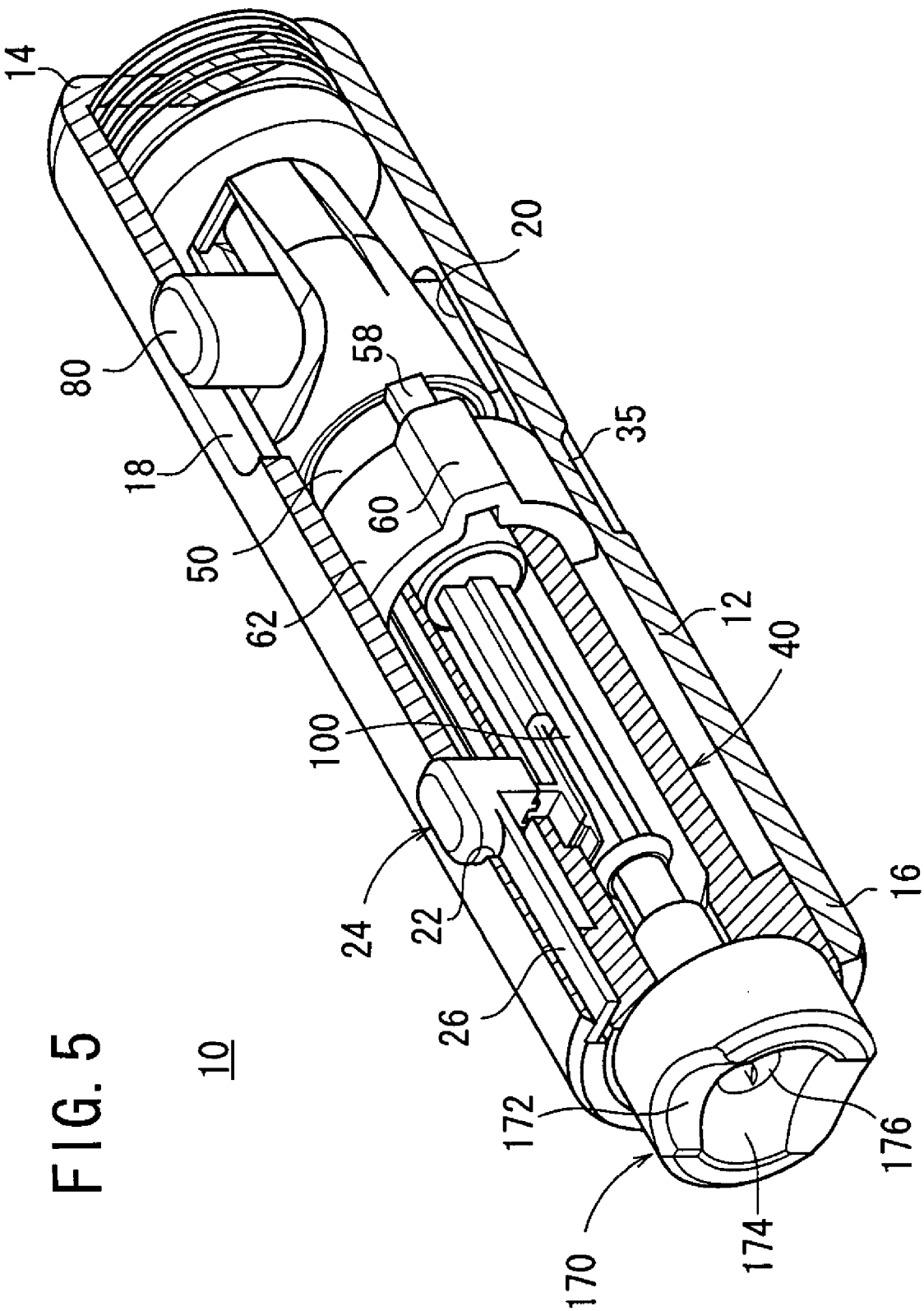
FIG. 5 is a perspective view, partly cut away, showing a drive mechanism of the puncture instrument shown in FIG. 3.

As shown in FIGS. 4 and 5, the adjusted member 50 includes a ridge 58 having a predetermined length along the axis of the inner tube 40 at a position perpendicular to the diametrical direction of the first oblong hole 18 and the second oblong hole 20. The depth adjustment knob 62 has a ridge 60 engaging the ridge 58 in covering relation to an outer surface thereof. The depth adjustment knob 62 comprises an arcuate thick member for adjusting the puncturing depth of the puncture needle of a puncture needle unit to be described later. The technical concept is disclosed in an invention "Puncture instrument" described in Japanese Laid-Open Patent Publication No. 2000-245717 and will not be described in detail below.

The ridge 60 of the depth adjustment knob 62 faces the fourth oblong hole 35 and can be turned circumferentially by a finger outside of the puncture instrument. Specifically, the depth adjustment knob 62 has an outer circumferential surface, except the ridge 60, held in sliding contact with the inner wall surface of the inner bore 34 of the outer tube 12. Thus, the depth adjustment knob 62 can be turned while being guided by the inner wall surface. Therefore, when the depth adjustment knob 62 is turned, the adjusted member 50 and the inner tube 40 integrally combined therewith are displaceable perpendicularly to the direction in which the depth adjustment knob 62 is turned.

A holder 70 is fixed to the one end 42 of the inner tube 40. The holder 70 is essentially shaped as a conical member projecting from the other end 44 toward the one end 42 and shaped as a tubular member near the one end 42. The conical member is represented by the reference character 72, the tubular member is represented by the reference character 74, and a stopper disposed within the conical member 72 is represented by the reference character 75.

The holder 70 has a diametrically extending space 76 formed therein between the conical member 72 and the tubular member 74. A recharging knob 80 is fixedly mounted in the space 76 and has an end exposed out of the first oblong hole 18 and the second oblong hole 20. Specifically, as shown in FIGS. 6 to 9, the recharging knob 80 has a tubular projection 82 on another side wall thereof which extends in the axial direction of the inner tube 40. The recharging knob 80 has a hole 84 formed therein which extends from an inside of the tubular projection 82 to the center of the recharging knob 80.

A disk 86 is secured to the tubular member 74 of the holder 70. The disk 86 is of a disk shape and has an outer circumferential wall held in sliding contact with the inner circumferential wall surface of the inner bore 34 of the outer tube 12. The disk 86 has a tubular projection 88 on a side surface thereof. A first resilient member (first biasing member), i.e., a first coil spring 92, is interposed between the disk 86 and the closed wall surface of the one end 14 of the outer tube 12. The first coil spring 92, which acts as a compression spring, produces resilient forces for normally pushing the recharging knob 80 from the one end 14 toward the other end 16.

A drive mechanism 100 is disposed in the inner bore 52 of the inner tube 40. The drive mechanism 100 includes an essentially flat shank body 102 having one end disposed in the tubular projection 88 which extends from the side surface of the disk 86 toward the recharging knob 80. The other end of the shank body 102 terminates in the other end 44 of the tubular body 46.

In the tubular projection 88, the one end of the shank body 102 is constructed as an arrowhead-shaped head 106 including a large-diameter portion engaged by a stopper 108. A second coil spring 110 as a second resilient member (second biasing member) is interposed between the stopper 108 and an end face of the tubular projection 82 in which the hole 84 is formed. The second coil spring 110 is a compression coil spring. The second coil spring 110 applies biasing forces tending to bias the shank body 102 of the drive mechanism 100 as a whole to be displaced toward the one end 14.

The shank body 102 has a projection 112 of substantially triangular cross section engageable with the stopper 75 on the conical member 72 of the holder 70.

Figure 6:
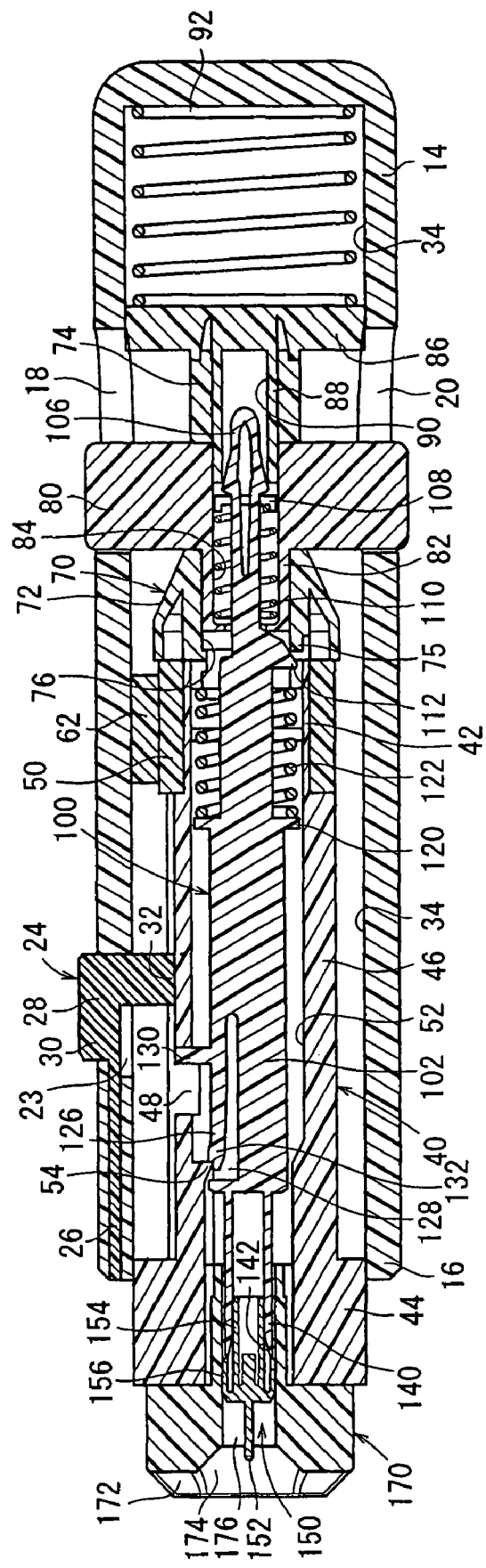
FIG. 6 is a longitudinal cross-sectional view of the puncture instrument shown in FIG. 3 which is in a state capable of a puncturing action.
Figure 7:
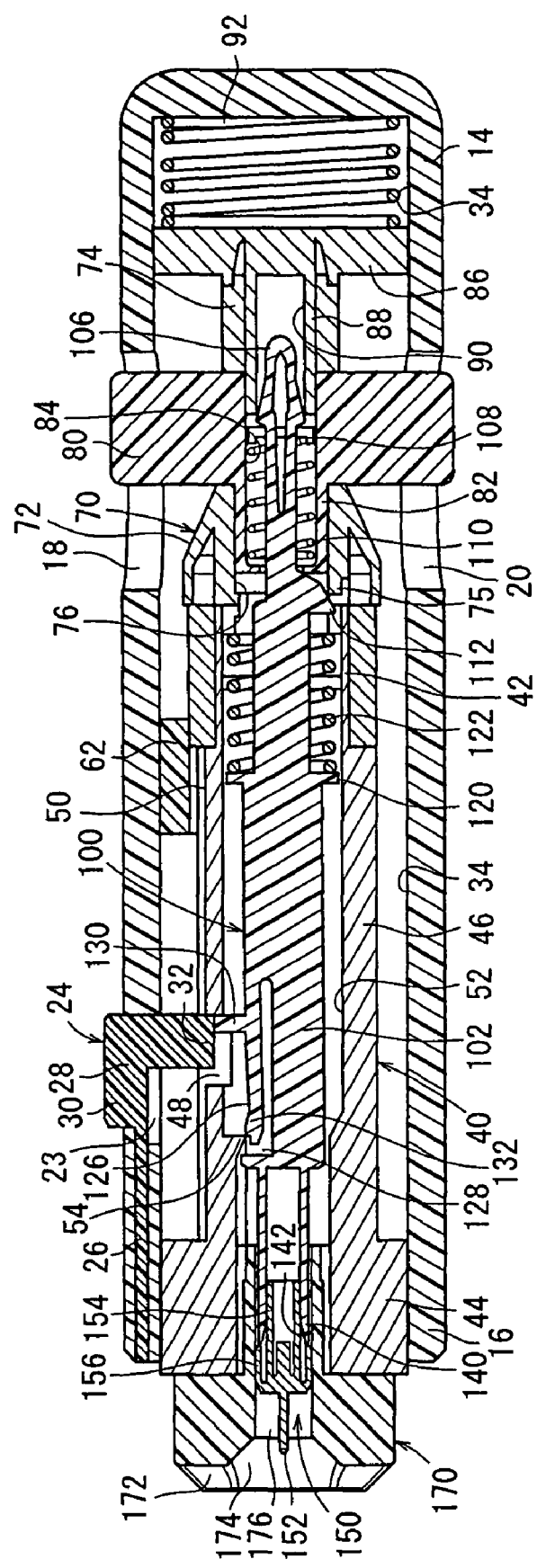
FIG. 7 is a longitudinal cross-sectional view of the puncture instrument shown in FIG. 3 which is in a state capable of a puncturing action when a push button is pushed.

As can easily be seen from FIG. 6, the shank body 102 has a flange 120 on an intermediate portion thereof. A third resilient member (third biasing member), i.e., a third coil spring 122, is interposed between the flange 120 and the conical member 72 of the holder 70. The third coil spring 122 is a compression coil spring as with the first coil spring 92 and the second coil spring 110.

The shank body 102 also has an engaging piece 126 near the other end 16. The engaging piece 126 is made flexible in directions perpendicular to the axis of the shank body 102, by a space 128 which is formed in the shank body 102. The engaging piece 126 is thus displaceable in the directions perpendicular to the axis of the shank body 102.

The engaging piece 126 includes a projection 130 having a distal end disposed in the hole 48 formed in the side wall of the inner tube 40. The engaging piece 126 has a distal end serving as an engaging end 132 having a bent groove complementary in shape to the engaging portion 54.

The shank body 102 includes a fitting member 140 for mounting the puncture needle unit, to be described below, in the vicinity of the area where the space 128 terminates. As can easily be seen from FIG. 6, the fitting member 140 has a distal end providing a slanted surface 142 oriented toward the axis of the shank body 102. The fitting member 140 may be tubular in shape, but should preferably be of a tongue piece shape for higher flexibility.

The puncture needle unit 150 will be described below.

The puncture needle unit 150 has a puncture needle 152 on its distal end and a tubular body 154 integral with the puncture needle 152. The tubular body 154 can be fitted in the fitting member 140 with predetermined frictional forces exerted therebetween. A skirt 156 is disposed around the tubular body 154 with a space formed therebetween. The skirt 156 is flexible and has a distal end which can contact the slanted surface 142 of the fitting member 140.

An abutting member 170 is disposed between the puncture needle unit 150 and the inner circumferential surface of the other end 44 of the inner tube 40. The abutting member 170, which is mounted in place from outside of the other end 44 of the inner tube 40, has a slanted surface 172 on its distal end which is largely concave perpendicularly to the axis of the cylindrical abutting member 170. The abutting member 170 also has a slanted surface 174 contiguous to the slanted surface 172 and continuous to an opening 176 which is formed in the abutting member 170 along the axis thereof. The puncture needle unit 150 enters the opening 176 and abuts against the slanted surface 142 of the fitting member 140 as described above. Since the skirt 156 resiliently abuts against the circumferential wall surface of the opening 176, the puncture needle unit 150 is normally not released from the abutting member 170.

The puncture instrument 10 according to the present embodiment is basically constituted as described above, and operation thereof will be described below.

The patient who wishes to measure its blood glucose level grips the outer tube 12 of the puncture instrument 10 with a right hand, for example. Preferably, the index finger is held in contact with the button body 28 of the puncture button 24 or more preferably the surface of the horizontal portion 30 of the puncture button 24. The patient then abuts the abutting member 170 on the distal end of the puncture instrument 10 against a region to be measured such as a hand, a finger, or an arm of the patient, and pushes the outer tube 12 toward the region against the resilient force of the first coil spring 92. The region to be measured of the patient now rises from the slanted surface 172 toward the slanted surface 174. The outer tube 12 is displaced relatively to the inner tube 40, during which time the horizontal end face of the vertical portion 32 of the puncture button 24 slides on the outer circumferential surface of the inner tube 40. During this time, the hand gripping the outer tube 12 feels the sliding movement on the outer circumferential surface. When the vertical portion 32 of the puncture button 24 substantially fully faces the hole 48 upon the sliding movement, the patient does not feel the sliding resistance from the outer circumferential surface of the inner tube 40 in coaction with the tongue piece 26. The patient now senses that the button body 28 can be pushed in the direction perpendicular to the axis of the outer tube 12.

The patient pushes the puncture button 24 with the index finger. Since the tongue piece 26 is flexible, the horizontal end face of the vertical portion 32 of the puncture button 24 pushes the projection 130 of the shank body 102 (see FIG. 7), bending the engaging piece 126 in the direction perpendicular to the axis.

Figure 8:
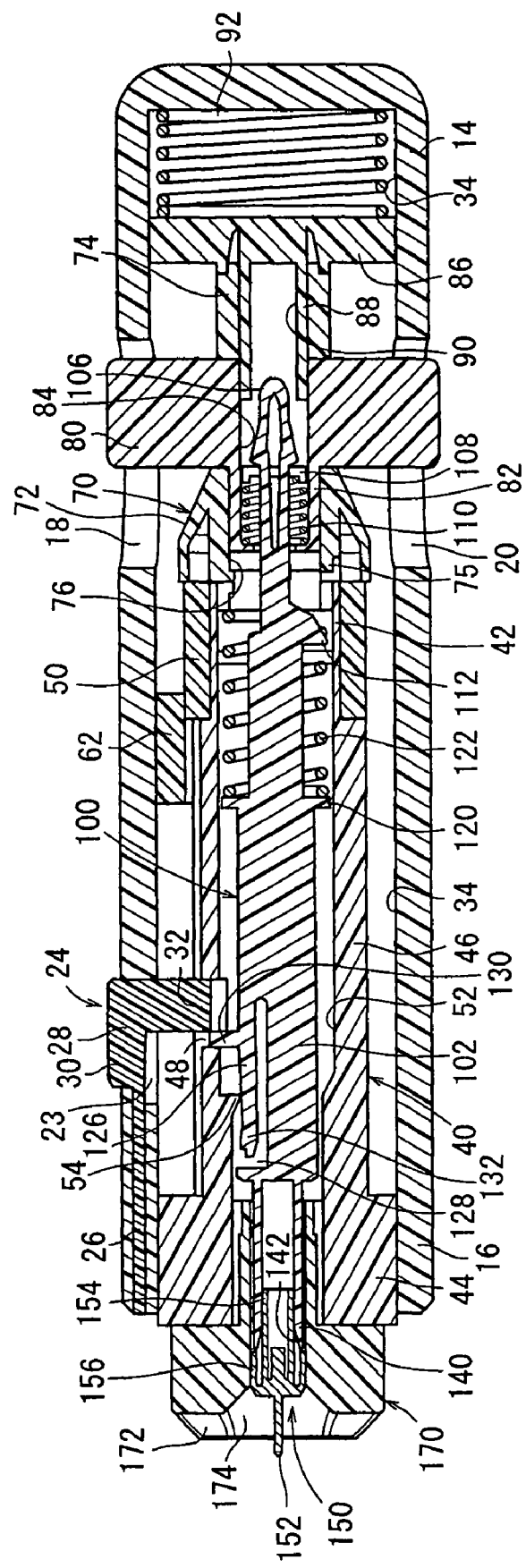
FIG. 8 is a longitudinal cross-sectional view of the puncture instrument shown in FIG. 3 which has a puncture needle projecting from an abutting member upon actuation of the drive mechanism.

The engaging end 132 is released from the engaging portion 54, whereupon the shank body 102 is instantaneously displaced toward the other end 16 under the resilient force of the third coil spring 122 against the compression force of the second coil spring 110 (see FIG. 8). Therefore, the puncture needle 152 of the puncture needle unit 150 mounted in the fitting member 140 of the shank body 102 projects from the opening 176, and punctures the hand, the finger, or the arm against which the patient is abutting the puncture instrument 10. Immediately thereafter, as the second coil spring 110 is compressed by the displaced stopper 108 mounted on the bottom of the head 106, the resilient force of the second coil spring 110 increases to forcibly displace the shank body 102 instantaneously toward the one end 14 (see FIG. 9).

Figure 9:
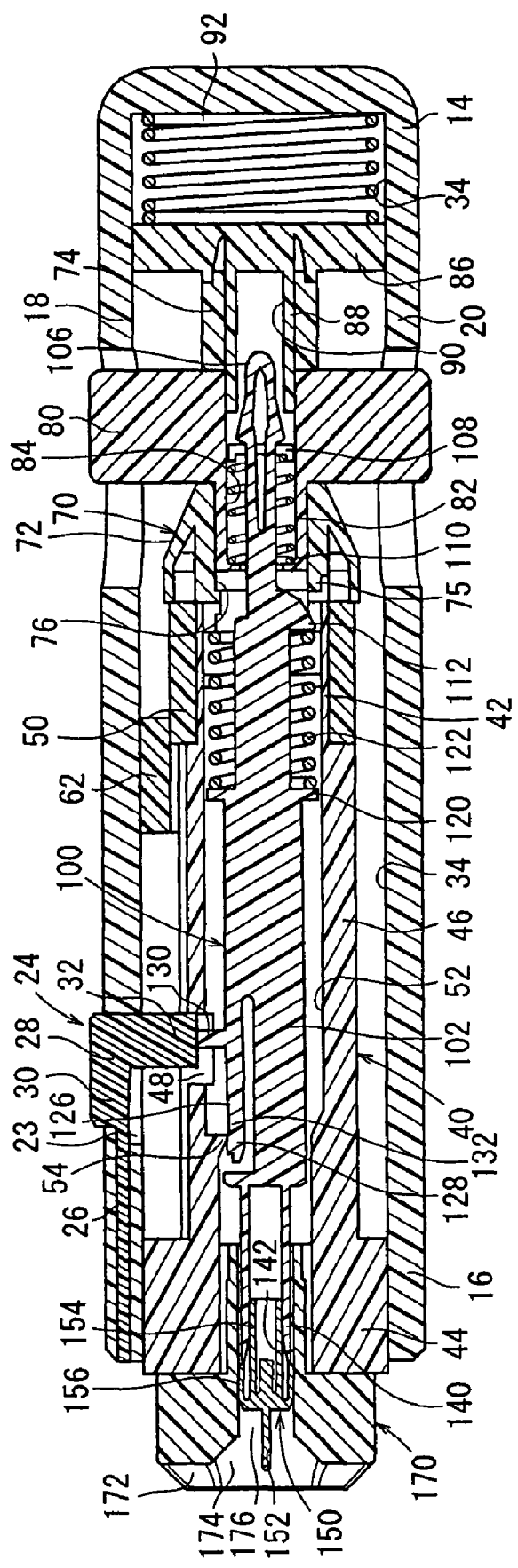
FIG. 9 is a longitudinal cross-sectional view of the puncture instrument shown in FIG. 3 with the drive mechanism being retracted.

In other words, the puncture needle unit 150 moves toward the region to be measures, e.g., the hand, the finger, or the arm of the patient, by the third coil spring 122, and is instantaneously retracted under the resilient force of the second coil spring 110 whose compressive force is released. Stated otherwise, as shown in FIG. 9, the shank body 102 moves to a position where the resilient force of the second coil spring 110 and the resilient force of the third coil spring 122 are balanced, whereupon the engaging end 132 abuts the tapered surface of the engaging portion 54.

A small amount of blood seeps out from the punctured region to be measured of the patient as it is pushed by the abutting member 170.

In order for an amount of blood which is sufficient for the measurement to seep out, the abutting member 170 may be pushed against the blood sampling region for a while. For prompting the patient to keep the outer tube 12 pushed toward the abutting member for a while after the patient is punctured, the puncture instrument 10 may have a continuous pushing prompter. The continuous pushing prompter may detect the time at which the patient is punctured, with a limit switch or the like, and produce a sound or turn on a lamp to notify the elapse of a predetermined time starting from the time at which the patient is punctured. When the continuous pushing prompter recognizes the elapse of the predetermined time with a given timer, the continuous pushing prompter turns off the sound or the lamp to notify to the patient that the time for which the outer tube 12 is to be pushed has elapsed.

Conversely, the continuous pushing prompter may produce a sound or turn on a lamp when the predetermined time has elapsed. Alternatively, the continuous pushing prompter may have a sensor or the like for monitoring the pushing force for the predetermined time after puncturing, and produce a sound or turn on a lamp to give a warning when the pushing force has dropped to a predetermined value. The continuous pushing prompter may specifically be a LED (Light Emitting Diode), a LCD (Liquid Crystal Display), a buzzer, an audio output unit, or the like. The continuous pushing prompter may notify the elapse of the predetermined time with at least one of tactile, visual, and auditory means.

The appropriate amount of blood thus obtained is transferred to a test paper, not shown, and processed by a measuring device for optically reading the blood glucose level thereof.

The outer tube 12 returns to the original position under the resilient force of the first coil spring 92 when the patient releases the puncture instrument 10 from the measured region. If the recharging knob 80 is displaced toward the one end 42, in particular, the puncture instrument 10 takes the position shown in FIG. 6. Besides, the puncture needle unit 150 is basically disposable. The puncture needle unit 150 may be removed from the abutting member 170, and a new puncture needle unit 150 may be mounted in the abutting member 170, whereupon the abutting member 170 may be inserted into the hole in the other end 44 of the inner tube 40. When the recharging knob 80 is displaced toward the one end 14, the engaging portion 54 engages with the bent groove in the engaging piece 126 to make the puncture instrument 10 ready for use.

The depth adjustment knob 62 is used to adjust the depth to which the patient is punctured. Specifically, when the depth adjustment knob 62 is turned upwardly or downwardly in FIGS. 3 to 5, the adjusted member 50 is turned to change the stop position of a stopper, not shown. By changing the stop position of the stopper, it is possible to adjust the position to which the region to be measured of the patient is to be punctured.

According to the present embodiment, when the vertical portion 32 of the puncture button 24 disengages from the outer circumferential wall of the inner tube 40 and reaches the hole 48, the patient can sense the shock with the fingertip. As the patient can confirm the arrival at the puncturing position, the patient may press the button body 28 with the finger. Since the patient can certainly puncture a desired portion where the abutting member 170 abuts, and especially, the patient can operate the puncture instrument 10 after having confirmed the timing to puncture the region to be measured, the patient can sample its blood stably with security.

The acquirement of the pressing force suitable for puncturing the region to be measured may be notified to the patient with at least one of tactile, visual, and auditory means.

According to the present embodiment, since the puncture instrument is of a simple structure, it can be handled with ease, can be used as a portable puncture instrument, and can be operated to puncture the patient whenever and wherever it needs to be used. As the puncture instrument is mechanical in nature, it operates reliably and hence gives the patient a feeling of security. The puncture instrument is inexpensive because as a whole it can be molded of synthetic resin except for the coil springs, and can conveniently be carried around by the patient because it is lightweight.

Since the puncture instrument is capable of obtaining an amount of blood required for measurement even when the patient is punctured to a small depth for minimizing pain, the annular (preferably conical) abutting member may be pressed against the surface of the living body with a small pushing force. Consequently, the puncture instrument can easily be handled by physically weak patients.

The puncture instrument 10 has been described above. The present invention is also applicable to a blood component measuring device 200 combined with a test paper and a measuring device, as shown in FIG. 10.

Figure 10:
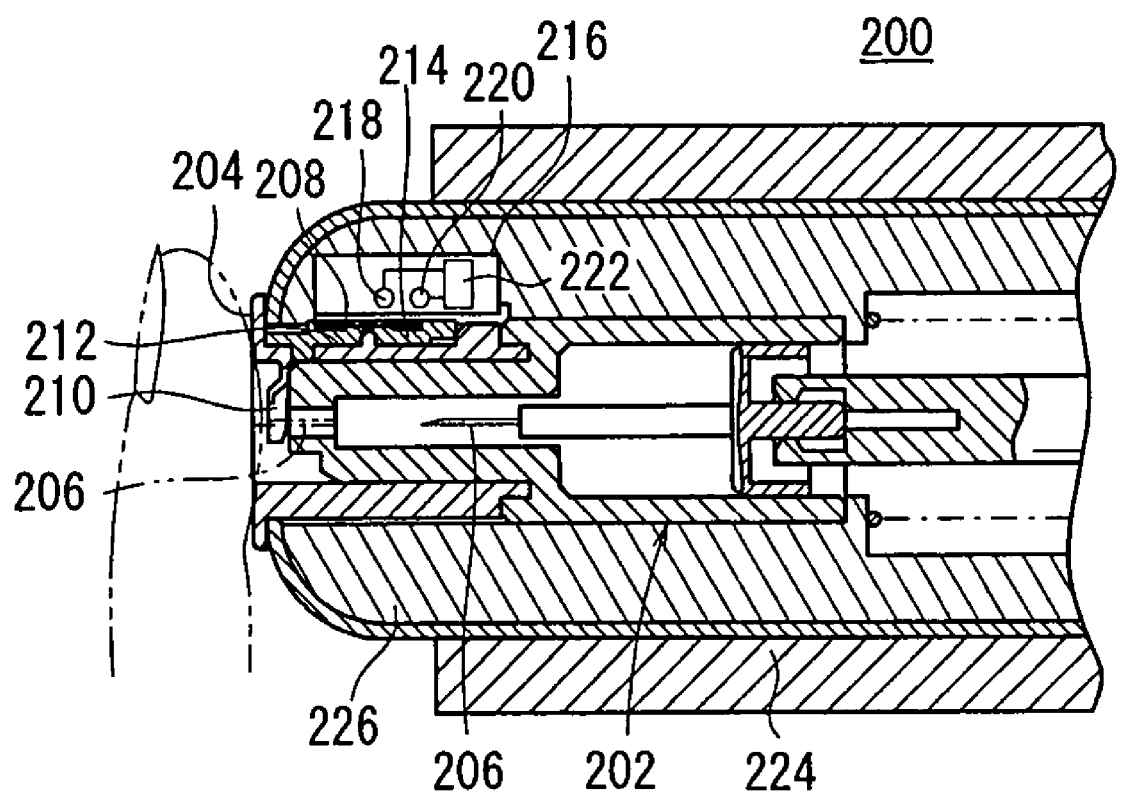
FIG. 10 is a cross-sectional view of a distal end of a blood component measuring device.

As shown in FIG. 10, the blood component measuring device 200 includes a tip 202 mounted in its distal end. The tip 202 has an abutting member 204 for abutting against the skin, a puncture needle 206, a test paper 208, a blood introducing guide 210, which is Y-shaped in front elevation (not shown), for guiding blood that seeps out when the skin is punctured from the punctured region to the test paper 208, and a narrow blood flow passage 212. The blood introducing guide 210 extends to contact the blood that seeps out from the skin. The blood is led to the blood introducing guide 210 under surface tension. Since the blood introducing guide 210 is Y-shaped, it does not present an obstacle to the movement of the puncture needle 206. The narrow blood flow passage 212 leads the blood to the test paper 208 through a capillary action.

The test paper 208 is held by a test paper holder 214 on a side of the tip 202. The test paper 208 is impregnated with a reagent containing a certain chromogenic agent and a buffer. The blood component measuring device 200 has an optical measuring unit 216 disposed in a position opposite to the test paper 208. The optical measuring unit 216 is controlled by a controller and comprises a light-emitting element 218, a light-detecting element 220, and an amplifier 222. The controller controls the light-emitting element 218 to emit light at suitable intervals and controls the light-detecting element 220 to detect the intensity of reflected light. When the test paper 208 is impregnated with blood, it produces a color, changing the intensity of the reflected light. The controller determines a blood glucose level or the like based on the change in the intensity of the reflected light, and displays the blood glucose level or the like.

The blood component measuring device 200 also includes an outer tube 224, an inner tube 226 mounted in the outer tube 224, and a puncture controller for allowing the puncture needle to puncture the skin surface when the pushing force applied to the skin surface by the abutting member 204 reaches a predetermined value or more. The puncture controller is of the same constitution as described above, and will not be described in detail below.

The blood component measuring device 200 may have a continuous pushing prompter as described above. For example, the controller may produce a sound or turn on a lamp when it detects that the test paper 208 is impregnated with blood based on a signal from the light-detecting element 220. Alternatively, the controller may measure a standard time that is spent after the skin is punctured until the blood reaches the test paper 208 (or a standard time until an appropriate amount of blood seeps out and contacts the blood introducing guide 210), and may produce a sound or turn on a lamp when the standard time has elapsed. When the controller detects that the pushing force applied to push the outer tube 224 is reduced, the controller may sound a predetermined warning.

The invention claimed is:

1. A puncture instrument comprising:
   a first tube;
   a second tube mounted in said first tube;
   a drive mechanism displaceably mounted in said second tube;
   a puncture needle unit disposed on a distal end of said drive mechanism and having a puncture needle;
   an abutting member for being pushed against a living body surface, said abutting member being disposed on a distal end of said second tube; and
   a puncture controller for allowing said puncture needle to puncture said living body surface when a pushing force applied to said living body surface by said abutting member reaches a predetermined value or more;
   wherein the puncture controller includes a push button disposed on the first tube for actuating a puncturing action only when the pushing force reaches the predetermined value or more.

2. A puncture instrument according to claim 1, wherein said puncture controller further includes a hole formed in said second tube for allowing said push button to be displaced, and wherein when said push button moves with said first tube along said second tube to said hole, said push button is displaceable into said hole, confirming that a pushing force applied to the living body surface has reached the predetermined value.

3. A puncture instrument according to claim 2, further comprising a first biasing member disposed in said first tube for biasing said second tube in a direction toward the distal end thereof, a second biasing member disposed in said second tube for displacing said drive mechanism in a direction toward a proximal end thereof, and a third biasing member disposed in said second tube for displacing said drive mechanism in the direction toward the distal end thereof.

4. A puncture instrument according to claim 3, further comprising a lock mechanism disposed on said drive mechanism for locking said drive mechanism on said second tube against a biasing force of said third biasing member and unlocking said drive mechanism from said second tube.

5. A puncture instrument according to claim 4, wherein said lock mechanism comprises a pushed member, said pushed member being capable of abutting against said push button through said hole, said drive mechanism having an engaging piece which is releasable from an engaging portion of said second tube to allow said drive mechanism to be displaced in the direction toward the distal end when said push button pushes said pushed member.

6. A puncture instrument according to claim 5, further comprising a notifying unit for notifying that the pushing force applied to said living body surface by said abutting member reaches the predetermined value or more, through at least one of tactile, visual, and auditory sensations.

7. A puncture instrument according to claim 6, wherein said notifying unit notifies that the pushing force applied to said living body surface by said abutting member reaches the predetermined value or more, through the tactile sensation based on a change in sliding resistance between said push button and said second tube.

8. A puncture instrument according to claim 1, wherein said puncture controller further comprises an electric control mechanism for controlling displacement of said drive mechanism.

9. A puncture instrument according to claim 8, wherein said electric control mechanism comprises a first switch for opening and closing an electric circuit depending on the position to which said second tube is displaced, a second switch actuatable by said push button, and an actuator for displacing said drive mechanism.

10. A puncture instrument according to claim 8, further comprising a notifying unit for notifying that the pushing force applied to said living body surface by said abutting member reaches the predetermined value or more, through at least one of tactile, visual, and auditory sensations.

11. A puncture instrument according to claim 1, further comprising a continuous pushing prompter for prompting a user to keep said abutting member pushed against said living body surface until an appropriate amount of blood seeps out of the living body surface after the living body surface is punctured.

12. A puncture instrument according to claim 1, further comprising a first biasing member disposed in said first tube for biasing said second tube in a direction toward the distal end thereof, a second biasing member disposed in said second tube for displacing said drive mechanism in a direction toward a proximal end thereof, and a third biasing member disposed in said second tube for displacing said drive mechanism in the direction toward the distal end thereof.

13. A puncture instrument according to claim 12, further comprising a lock mechanism disposed on said drive mechanism for locking said drive mechanism on said second tube against a biasing force of said third biasing member and unlocking said drive mechanism from said second tube.

14. A puncture instrument according to claim 1, further comprising a notifying unit for notifying that the pushing force applied to said living body surface by said abutting member reaches the predetermined value or more, through at least one of tactile, visual, and auditory sensations.

* * * * *